United States Patent
Shreve et al.

(10) Patent No.: US 9,126,164 B2
(45) Date of Patent: Sep. 8, 2015

(54) VALVE SWITCH MODULATION FOR REDUCING ERRORS DUE TO OSCILLATIONS OF THE INLET FLUID OF A PUMP SYSTEM

(71) Applicant: Waters Technologies Corporation, Milford, MA (US)

(72) Inventors: Joshua A. Shreve, Franklin, MA (US); Steven J. Ciavarini, Natick, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/521,514

(22) Filed: Oct. 23, 2014

(65) Prior Publication Data

US 2015/0043303 A1 Feb. 12, 2015

Related U.S. Application Data

(63) Continuation of application No. 14/093,836, filed on Dec. 2, 2013, now Pat. No. 8,894,274, which is a continuation of application No. 13/949,806, filed on Jul. 24, 2013, now Pat. No. 8,622,609, which is a (Continued)

(51) Int. Cl.
*B01F 13/00* (2006.01)
*B01F 15/04* (2006.01)
*G01N 30/34* (2006.01)

(Continued)

(52) U.S. Cl.
CPC .......... *B01F 15/0479* (2013.01); *B01D 15/14* (2013.01); *B01F 15/0216* (2013.01); *G01N 30/34* (2013.01); *G01N 35/00871* (2013.01); *G01N 30/36* (2013.01);

(Continued)

(58) Field of Classification Search
CPC .............. F04B 49/065; B01F 15/0479; B01F 15/0216; B01F 15/14; G01N 30/34; G01N 35/00871; G01N 35/1097
USPC ..................... 417/53; 222/132; 366/348, 349
See application file for complete search history.

(56) References Cited

U.S. PATENT DOCUMENTS

| 3,985,019 A | 10/1976 | Boehme et al. |
| 4,595,496 A | 6/1986 | Carson |

(Continued)

OTHER PUBLICATIONS

International Search Report and Written Opinion in related international patent application No. PCT/US2009/056434, mailed on Oct. 30, 2009.

*Primary Examiner* — Tony G Soohoo
*Assistant Examiner* — Anshu Bhatia
(74) *Attorney, Agent, or Firm* — Schmeiser, Olsen & Watts LLP; William G. Guerin

(57) ABSTRACT

Described is a method of reducing liquid composition errors in a low-pressure mixing pump system. Packets representing the switching intervals of each component of the desired fluid mixture are provided to an intake of the mixing pump system. For each packet, a switching time associated with at least one of the components in the packet is modulated. Modulated switching times are based on time offsets that are specifically selected according to the undesirable frequency characteristic of an intake response of the mixing pump system. The average of the volumes contributed by the packets thus modulated is equal to a component volume that achieves a desired proportion of the component in the output flow of the mixing pump system. Modulated switching times enable the reduction or elimination of composition error in the output flow of the mixing pump system.

2 Claims, 10 Drawing Sheets

Related U.S. Application Data continuation of application No. 13/063,382, filed as application No. PCT/US2009/056434 on Sep. 10, 2009, now Pat. No. 8,517,597.

(60) Provisional application No. 61/096,480, filed on Sep. 12, 2008.

(51) Int. Cl.
*G01N 35/00* (2006.01)
*B01F 15/02* (2006.01)
*B01D 15/14* (2006.01)
*G01N 30/36* (2006.01)
*G01N 35/10* (2006.01)

(52) U.S. Cl.
CPC ..... *G01N 35/1097* (2013.01); *G01N 2030/347* (2013.01); *G01N 2035/00544* (2013.01)

(56) References Cited

U.S. PATENT DOCUMENTS

| | | | |
|---|---|---|---|
| 4,767,279 | A | 8/1988 | Dourdeville et al. |
| 6,893,547 | B2 | 5/2005 | Gascoyne et al. |
| 7,048,512 | B2 * | 5/2006 | Couillard et al. ............ 417/53 |
| 2002/0134143 | A1 | 9/2002 | Allington et al. |

* cited by examiner

VALVE SWITCH MODULATION FOR REDUCING ERRORS DUE TO OSCILLATIONS OF THE INLET FLUID OF A PUMP SYSTEM

RELATED APPLICATIONS

This application is a continuation patent application of U.S. patent application Ser. No. 14/093,836, filed Dec. 2, 2013, which is a continuation patent application of U.S. patent application Ser. No. 13/949,806, now U.S. Pat. No. 8,622,609, filed Jul. 24, 2013, which is a continuation patent application of U.S. patent application Ser. No. 13/063,382, now U.S. Pat. No. 8,517,597, filed May 11, 2011, which is the national stage of International Application No. PCT/US2009/056434, filed Sep. 10, 2009 and designating the United States, which claims benefit of and priority to U.S. Provisional Patent Application No. 61/096,480, filed Sep. 12, 2008. The contents of these applications are expressly incorporated herein by reference in their entireties.

FIELD OF THE INVENTION

The invention relates generally to switching valves in liquid pump systems. More particularly, the invention relates to a method for reducing errors resulting from the intake fluid behavior of a gradient proportioning valve in a low pressure gradient pump system for liquid chromatography.

BACKGROUND OF THE INVENTION

A variety of applications exist in which the need to meter two or more liquids in accurately controlled proportions is critical. One such application is liquid chromatography wherein an analyte sample is passed in a flow of liquid solvent (the mobile phase) through a column packed with particulate matter (the stationary phase). While passing through the column, the various components in the sample separate from one another by adsorbing and desorbing from the stationary phase at different rates such that the individual components elute from the column at different times. The separated components flow through a detector which responds to each component and provides information to the user about the constituents of the sample.

To achieve more effective separations, high performance liquid chromatography (HPLC) systems often use mixtures of solvents as the mobile phase. When this mixture is held constant, the system operates in an isocratic mode. More conventionally, the system operates in a gradient mode whereby the components of the mixture are changed over time.

As used herein, a packet means a sequential contribution of fluid components provided to the pump intake. FIG. 1 graphically depicts an example of two consecutive packets where each packet includes contributions from a first solvent A, then a second solvent B, then a third solvent C and finally a fourth solvent D. A slice as used herein means the contribution of a single component to a packet. Thus the volume of component A in each packet is the first slice for the packet, the volume of component B in each packet represents the second slice for the packet, and so forth.

During gradient chromatography, metering and accuracy of the pump system is dependent on the valves controlling the volume of fluid drawn into the pump for each slice. Conventional metering techniques are based on an intake flow that accurately follows the commanded flow; however, the intake flow typically behaves like an underdamped system. FIG. 2 shows an example of the flow error due to the switching of a valve. As illustrated, the flow error is a decaying sinusoid. The flow errors for a given system vary according to the gas solubility, viscosity, and compliance of the solvents and other factors relating to hydraulic inertia. Subsequent switching of the valves typically results in errors in the relative proportions of the components unless the switching occurs at a zero error crossing. Moreover, each additional switching event similarly results in a new intake flow disturbance and corresponding flow error that can adversely affect the desired proportions of components.

Thus liquid chromatography performance being greatly dependent on the compositional accuracy of the solvent mixture is typically limited by errors due to the system intake response of the pump system and proportioning valve. The present invention addresses the need to reduce these errors.

SUMMARY

The invention relates to a method for reducing composition error in the output flow of a low pressure mixing pump system due to the intake behavior of the pump system. Actuation of the switching valves for one or more of the components vary in time with respect to the initiation of a packet. This modulation of the actuation times and the consequential modulation of corresponding component volumes are performed in a manner that preserves the average of the component volumes to achieve the desired proportions in the output flow of the pump system. The modulation pattern is specifically selected according to frequency characteristics of the intake response of the pump system to reduce or cancel related errors.

In one aspect, the invention features a method of reducing composition error in the output flow of a mixing pump system. The method includes actuating a first valve during a first packet to provide a first volume of a first component to an intake of the mixing pump system. A second valve is actuated during the first packet to provide a first volume of the second component to the intake of the mixing pump system. The first valve is actuated for at least one subsequent packet to provide an additional volume of the first component to the intake of the mixing pump system. The second valve is actuated for at least one subsequent packet to provide an additional volume of the second component to the intake of the mixing pump system, wherein at least two of the first and additional volumes of the first component differ and at least two of the first and additional volumes of the second component differ.

In another aspect, the invention features a mixing pump system having reduced composition error in an output flow. The mixing pump system includes a gradient proportioning valve, a pump and a system controller. The gradient proportioning valve has an outlet port and a plurality of fluid switching valves each adapted for providing a component to an intake flow. The pump has an inlet port coupled to the outlet port of the gradient proportioning valve. The system controller is in communication with the gradient proportioning valve and the pump. The system controller provides a signal to the gradient proportioning valve to actuate the fluid switching valves at modulated switching times. The modulated switching times are determined from a plurality of switching time offsets which are determined in response to a frequency characteristic of an intake response of the mixing pump system.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

In brief overview, the invention relates to a method for reducing composition error in the output flow of a low pressure mixing pump system due to the intake behavior of the pump system. Actuation of the switching valves for one or more of the components vary in time with respect to the initiation of a packet. This modulation of the actuation times and the consequential modulation of corresponding component volumes are performed in a manner that preserves the average of the component volumes necessary to achieve the desired proportions. The modulation pattern is specifically selected according to frequency characteristics of the intake response of the pump system to reduce or cancel related errors. The method produces predictable results that do not vary in time.

In the following description, the switching of proportioning valves is generally specified with respect to time; however, in preferred embodiments switching is referenced to the volume domain according to component volume. For example, switching events may be indexed to pump stroke displacement or stepper motor position so that variations from a constant inlet flow rate can be accommodated.

Figure 1:
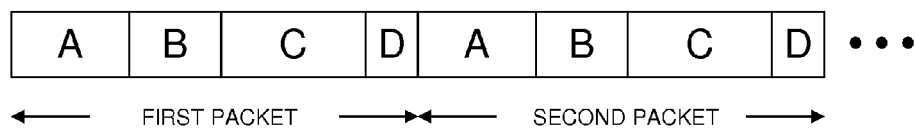
FIG. 1 is an illustration of an example of two consecutive packets composed of slices.
Figure 3:
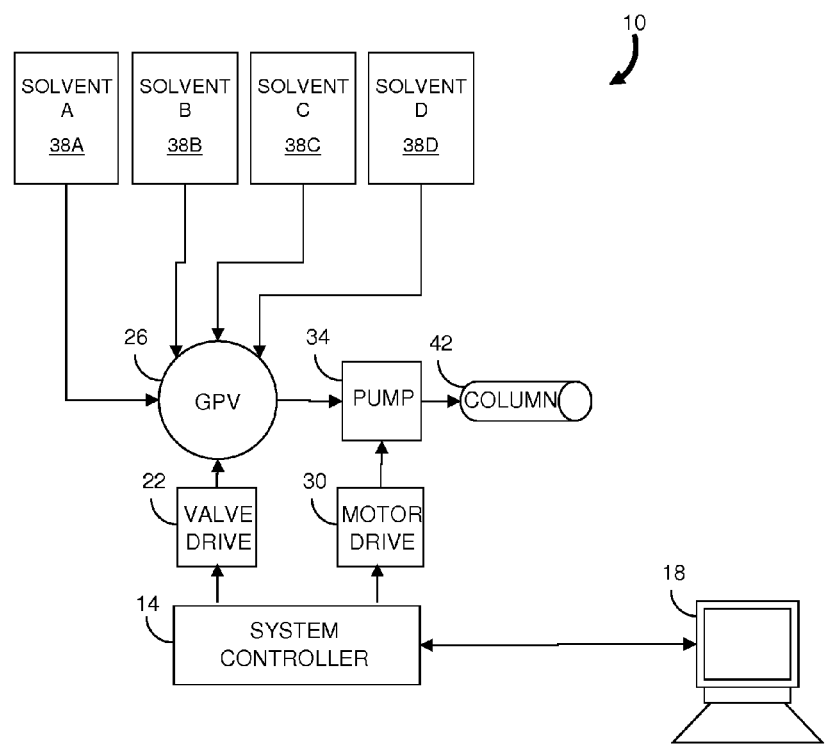
FIG. 3 is a block diagram of a liquid chromatography system that can be used to practice an embodiment of the method of the invention.

FIG. 3 is a block diagram of a liquid chromatography system 10 that can be used to practice the method of the invention. The system 10 includes a system controller 14 (e.g., microprocessor) in communication with a user interface device 18 for receiving input parameters and displaying system information. The system controller 14 communicates with a valve drive module 22 for operating a gradient proportioning valve (GPV) 26 and a motor drive module 30 for operating one or more stepper motors for a pump system 34. The pump system 34 can include complementary pump heads that are operated in opposite phase as is known in the art. The gradient proportioning valve 26 includes a plurality of fluid switching valves which are in turn connected by tubing to respective component reservoirs 38A, 38B, 38C, 38D that hold the components (solvents) to be combined. The fluid switching valves of the gradient proportioning valve 26 are coupled through a common outlet port which in turn is connected to the inlet port of the pump system 34. The outlet port of the pump system 34 delivers the mixture of solvents to a chromatographic column 42, typically at much higher pressures.

During operation of the liquid chromatography system, the switching valves of the gradient proportioning valve 26 are opened sequentially so that the pump system 34 draws liquid from each of the reservoirs 38. The proportions of solvents present in the liquid mixture delivered by the pump system 34 depend on the relative actuation time of each of the switching valves in relation to the inlet velocity profile during the intake cycle.

Figure 2:
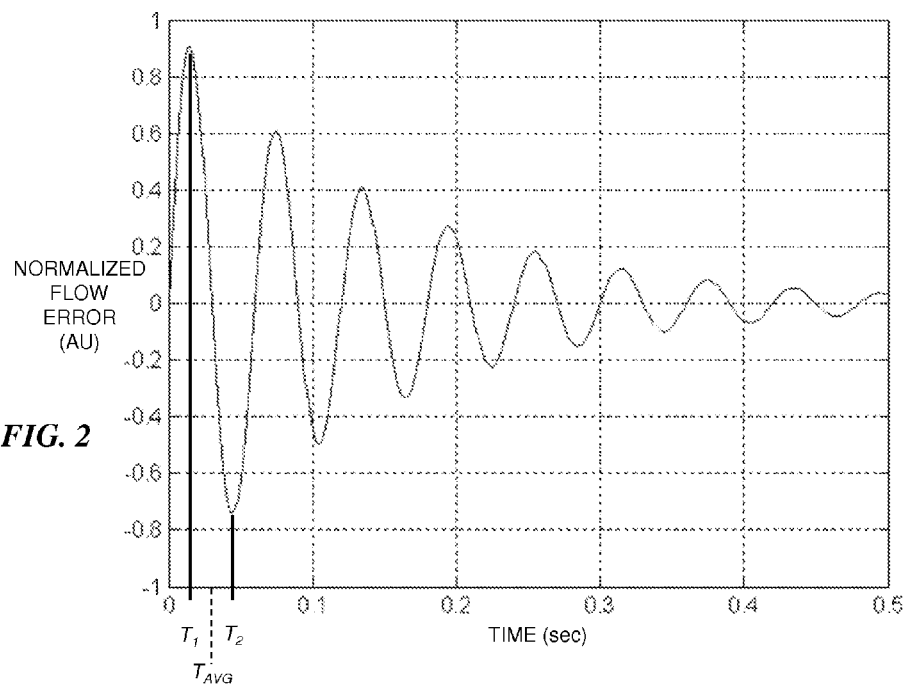
FIG. 2 graphically illustrates flow error resulting from the switching of a valve.

As described above, the initiation of intake for a pump typically results in the start of an intake response as shown in FIG. 2 where an error occurs in the desired intake flow rate. According to the method of the invention, switching times (i.e., the times at which the switching valves are actuated) are carefully determined so that the volume contributions for each slice of a given solvent average to a desired value. These switching times are offset in time from switching times used in a conventional pump system in which the error in the intake flow rate due to the intake response is ignored or left uncompensated.

In one embodiment of the method, if a dominant frequency appears in the intake response as depicted in FIG. 2, a two-point offset modulation of the switching times is used to target the dominant frequency and thereby significantly reduce the error. Instead of operating the switching valve at the proportioned time after each packet initiation time, as with a conventional pump system, the switching valve is actuated early by one-quarter of the period of the sinusoid and on the next packet, the switching valve is actuated late by one-quarter of the period of the sinusoid. The earlier switching time $T_1$ is used for the first slice of the solvent and the later switching time $T_2$ is used for the slice of the solvent in the next packet. Switching times $T_1$ and $T_2$ are alternated for subsequent packets. Thus the volume of the solvent introduced in the slice starting at the earlier switching time $T_1$ is slightly greater than the amount necessary to maintain the desired proportion of solvents; however, the volume of the solvent introduced in the slice for the next packet starting at the later switching time $T_2$ is slightly less than the proper amount. Consequently, the average volume of the solvent remains unchanged from that of an unmodulated pump system with no flow error. In a complementary manner, the volume of a solvent in the slice that immediately precedes the modulated switching events is first less than and then subsequently greater than the desired volume for that solvent such that its average volume is also the same as the volume of that solvent for a slice in an unmodulated pump system with no flow error. For embodiments in which the offset modulation uses three or more modulation points, there is no requirement for complimentary offset times as in the two-point offset modulation scheme; however, the average contributions of the solvents after utilizing all the modulation points are the same as the volumes of the solvents for respective slices in an unmodulated pump system without flow error.

Figure 4:
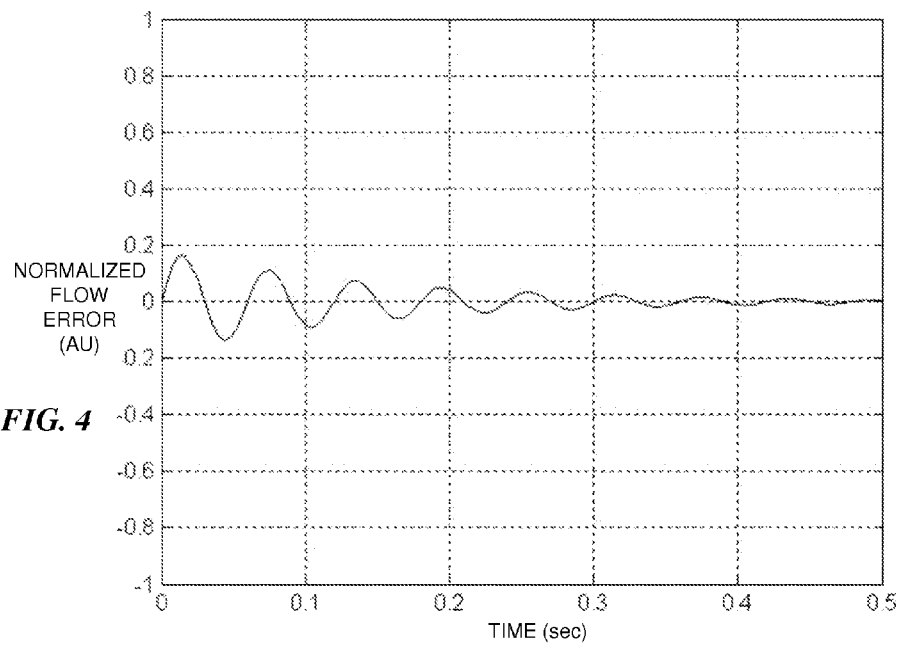
FIG. 4 illustrates the reduction of flow error in comparison to the flow error of FIG. 2 resulting from switching time offset modulation according to an embodiment of the invention.

Although the times $T_1$ and $T_2$ are shown in the example based on FIG. 2 to correspond to a maximum flow error and a subsequent minimum flow error, in other embodiments the switching times occur at other positions (times) in the intake response, although the difference in the switching times $T_1$ and $T_2$ remains the same. FIG. 4 illustrates how this error varies in time for other positions of $T_1$ and $T_2$ relative to the intake response. Due to the decaying nature of the sinusoidal intake response, the error is generally not completely eliminated; however, the error is generally much less than the error that occurs in a system without switching time modulation. In effect, the determination of the switching times according to the invention is based on digital filtering. For a two-point modulation scheme the digital filter targets the dominant frequency of the sinusoidal intake response. In this case, the difference between times $T_1$ and $T_2$ is half the period of the sinusoidal intake response.

In general, a more complex pattern of switching to accommodate a range of frequencies present in an intake response is preferred. The switching time offsets correspond to a digital filter implementation where the offsets are selected to achieve the desired filter frequency characteristic. Using more switching time offsets generally enables better filter frequency control; however, more switching time offsets requires more time to achieve the proper volume averages and therefore can make mixing more difficult. The sum of the switching time offsets are zero so that the average of the switching times matches the switching time in an unmodulated system with no flow error. Consequently, the desired solvent proportions are achieved. In effect, the method of the invention is based on a tradeoff: compositional noise is introduced to the pump system by inducing offsets in the switching times; however, the accuracy of the pump system as measured according to component volumes is improved.

Figure 5:
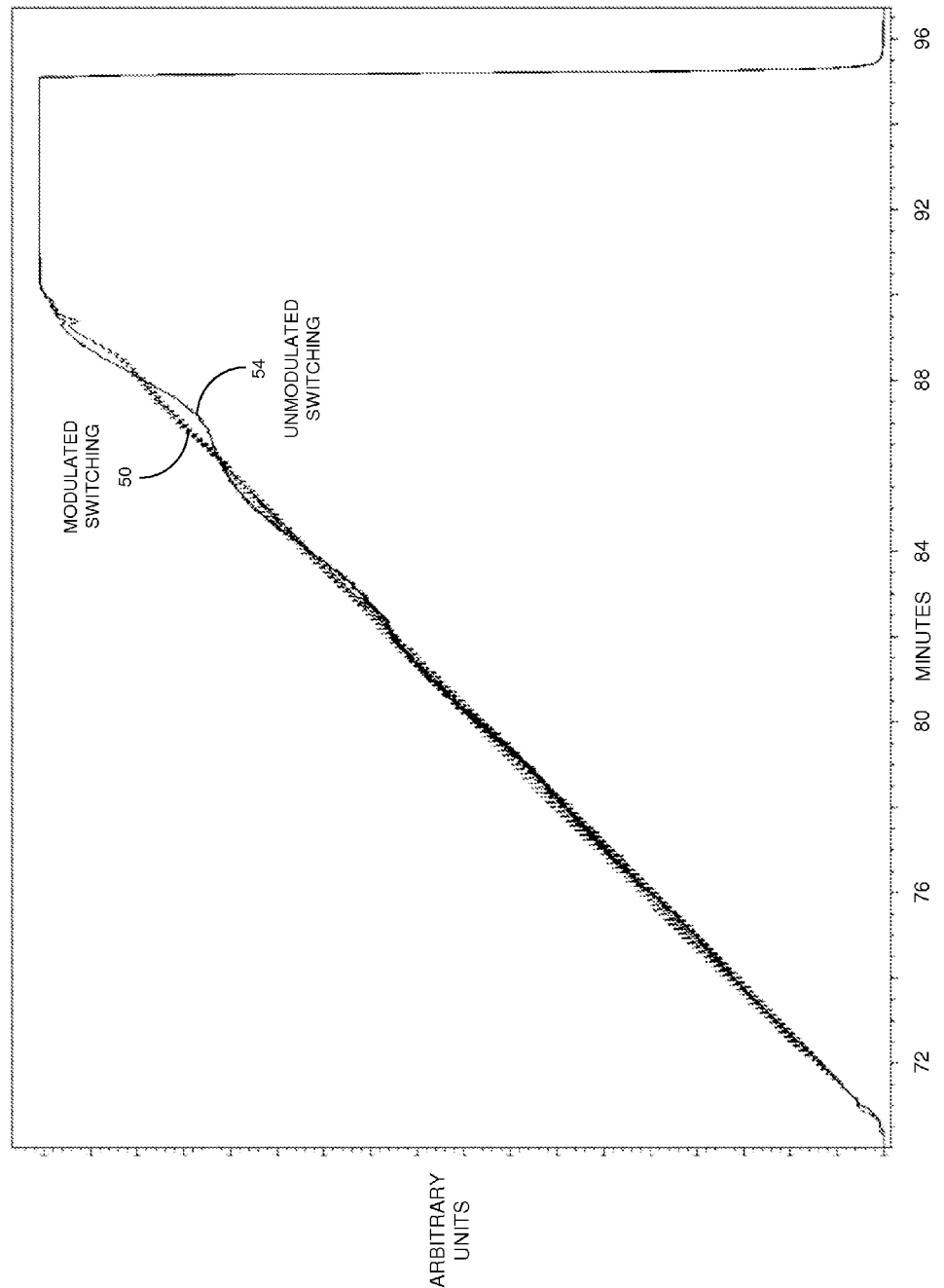
FIG. 5 graphically illustrates examples of a binary gradient for unmodulated switching times and a binary gradient achieved using modulated switching times according to an embodiment of the method of the invention.

FIG. 5 shows an example of a linear gradient for a two solvent liquid phase (i.e., a binary gradient). The line 50 indicates the gradient achieved using a gradient proportioning valve with modulated switching times according to the method of the invention. The line 54 indicates the gradient achieved using a gradient proportioning valve with fixed (unmodulated) switching times. Although high frequency deviations from a linear gradient are observable for the modulated gradient 50, these deviations are small with respect to deviation from a linear gradient for the unmodulated system.

Figure 6A:
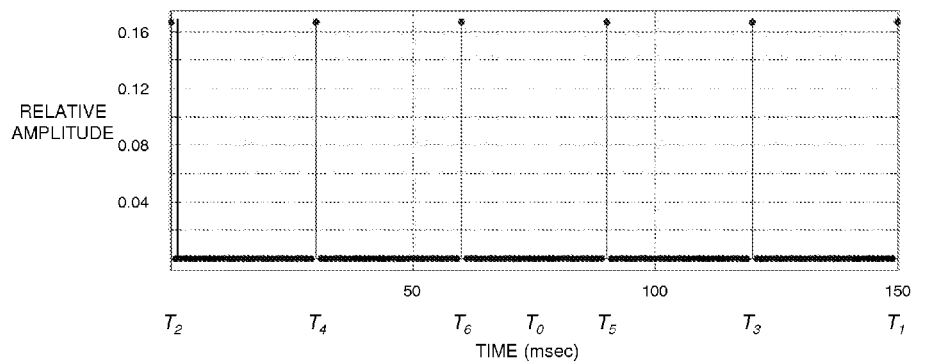
FIGS. 6A and 6B graphically illustrate a six-point modulation scheme and the corresponding frequency response according to an embodiment of the invention.
Figure 6B:
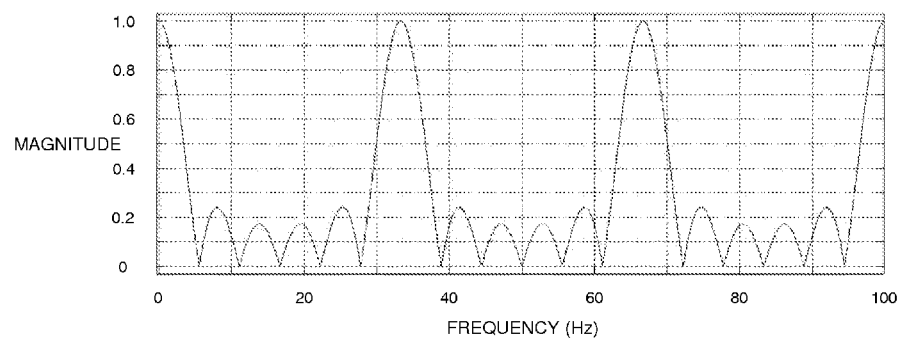

The desired frequency characteristic of the digital filter is determined by measurement for a range of solvents of interest and the switching times are selected based on the determined frequency characteristic. FIG. 6A shows an example of a six-point modulation scheme and FIG. 6B shows the corresponding frequency response. Switching is performed in sequence at the times $T_1, T_2, T_3, T_4, T_5$ and $T_6$. The unmodulated switching time $T_0$ for a conventional pump system is shown for comparison and is the same as the average for the modulated switching times. Times $T_1, T_3$ and $T_5$ represent delayed switching relative to the average switching time $T_0$ and times $T_2, T_4$ and $T_6$ are advanced relative to the average switching time $T_0$.

The switching time offsets shown in FIG. 6A are symmetrically distributed about the average switching time $T_0$ so that the number of advanced switching events equals the number of delayed switching events. In other embodiments the number of switching time offsets can be odd so that there is no symmetry about the average switching time $T_0$, although the average switching time is maintained at $T_0$. Preferably, the switching time offsets are implemented in an order such that the average of any two switching time offsets is approximately zero to better shape the noise introduced in the modulation process.

Figure 7:
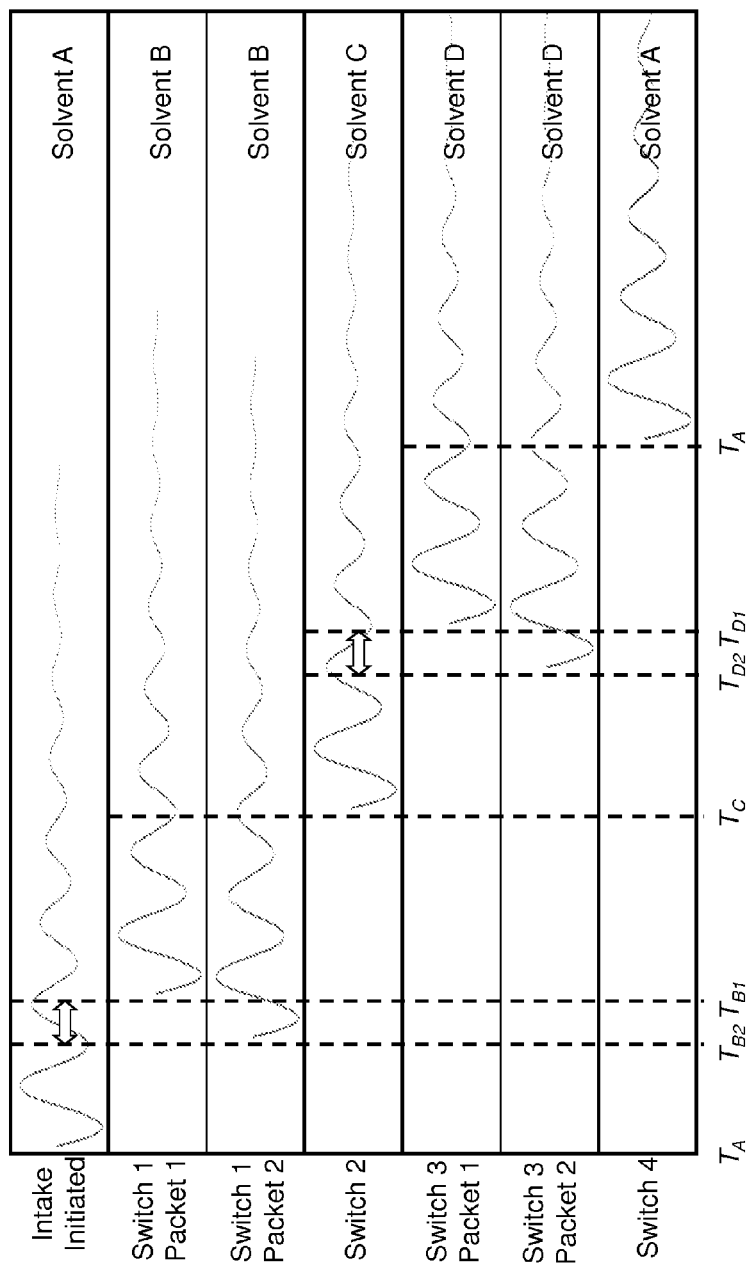
FIG. 7 is a timeline depicting an embodiment of the method of the invention using a two-point modulation scheme to control the switching of four solvents.

FIG. 7 is a timeline depiction for an embodiment of the method of the invention using a two-point modulation scheme. As illustrated, the method is used to control the switching of four solvents A, B, C and D per packet with one packet occurring for each pump stroke. Actuation of each switch to provide the corresponding solvent results in an intake response in the form of a decaying sinusoid as described above. On a first pump stroke, actuation of switch 1 for solvent B occurs at time $T_{B1}$ and results in the intake response labeled Switch 1-Packet 1. On the next pump stroke, actuation of switch 1 for solvent B occurs at time $T_{B2}$ and results in the intake response labeled Switch 1-Packet 2. The two offset intake responses resulting from the modulation of switch 1 for solvent B permits switch 2 for solvent C to be unmodulated. More specifically, a first actuation of switch 2 at time $T_C$ occurs at a relative low point in the Switch 1-Packet 1 intake response of solvent B and the next actuation of switch 2 during the next packet at time $T_C$ occurs at a relative high point in the Switch 1-Packet 2 intake response. Effectively, the actuation time of switch 2 is modulated with respect to the intake response of solvent B in an alternating manner about an average value without actually changing the modulation time $T_C$ relative to the intake initiation time $T_A$. Thus the variation of the volume for each slice of solvent B is due only to the modulation of switch 1. As switch 2 has no offset modulation, the actuation time $T_D$ of switch 3 is modulated to prevent the intake response for solvent D from always starting at the same position along the intake response of solvent C. As shown, switch 3 actuates first at a time $T_{D1}$ and then during the next packet at a time $T_{D2}$ with further switch actuations for subsequent packets occurring in an alternating fashion.

It should be recognized that the switching time modulation described with reference to FIG. 7 can be extended in a more general sense to any number of solvents. In particular, switching time modulation is applied to the switches providing "even solvents" (e.g., solvent B and solvent D) while no modulation of the switching times is necessary for "odd solvents" (e.g., solvent A and solvent C).

The method of the invention can be described more generally as follows. The switching time offsets d are defined by a vector having n elements each indicating a switching time offset value $(d_1, d_2, d_3, \ldots, d_n)$. m is a variable representing the index of the elements of the vector. Once all switching time offsets values d are used (i.e., m>n), the values d are used again in order starting with $d_1$, (i.e., m=(m mod n)+1).

The method is applied according to either of two rules where the particular rule selected is determined according to the number of packets per pump stroke and the number of slices per packet. The first rule is applied if the number of packets per pump stroke does not exceed one or if the number of slices per packet is an even number. According to the first rule, modulation is performed for the first switching event and every other switching event in a pump stroke. The occurrence of a new pump stroke resets the counting of the switching events for a pump stroke. For each new packet, the next value in sequential order in the switching time offset vector is used.

FIG. 8A to FIG. 8H illustrate the application of the first rule for different values of packets per pump stroke (PpS) and slices per packet (SpP). Dashed vertical lines are used to show the initiation of a pump stroke. Hashed areas depicted under the switching time offset "$d_n$" are used to indicate the increase and decrease in time and volume for the adjacent slices.

Figure 8A:
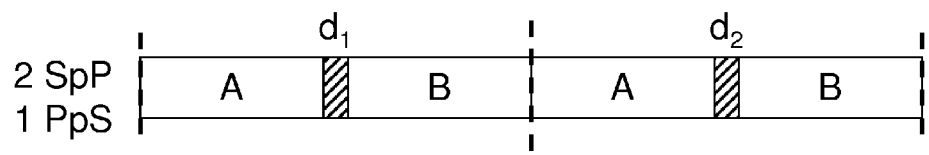
FIGS. 8A to 8H illustrate the application of an embodiment of the method of the invention according to a first rule for different values of packets per pump stroke and slices per packet.
Figure 8B:
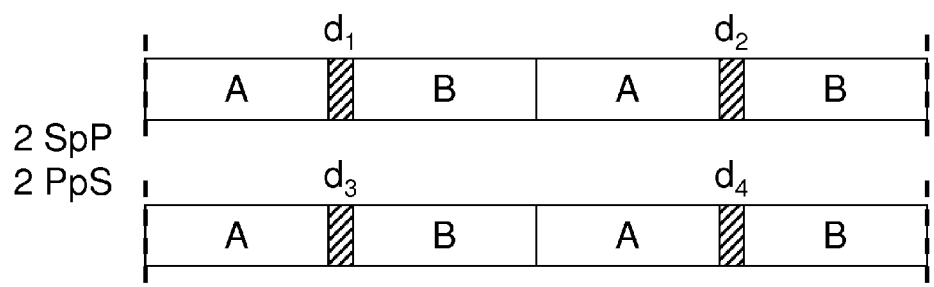
Figure 8C:
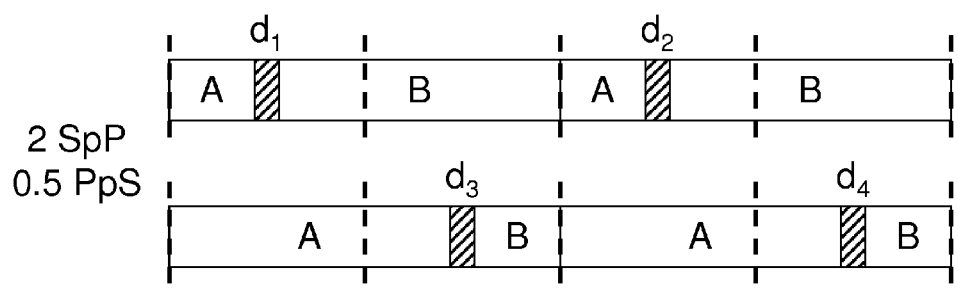
Figure 8D:
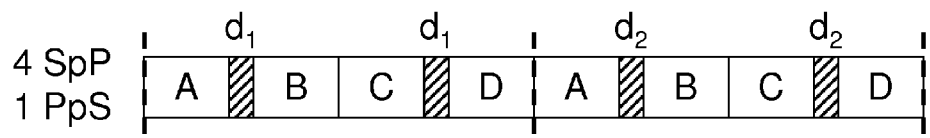
Figure 8E:
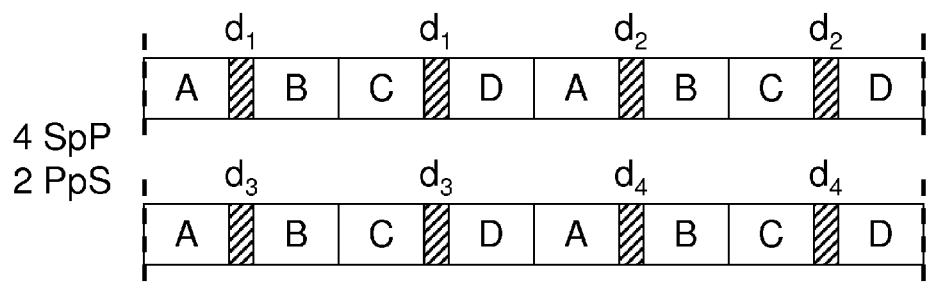
Figure 8F:
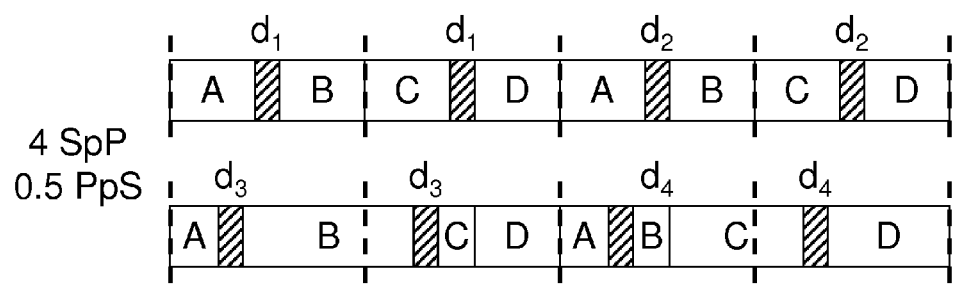
Figure 8G:
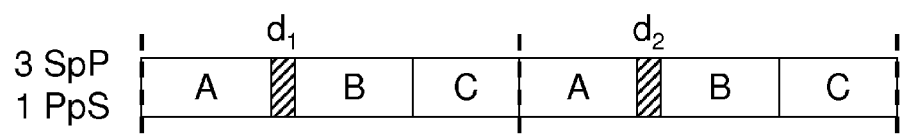
Figure 8H:
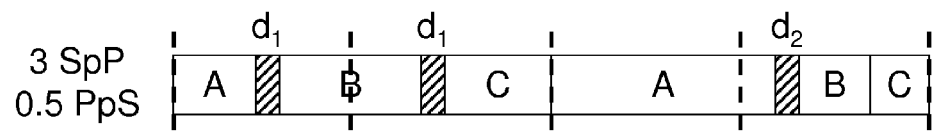

FIG. 8A illustrates one packet per pump stroke and two slices per packet, and FIG. 8B illustrates two packets per pump stroke and two slices per packet. FIG. 8C illustrates one-half packet per pump stroke and two slices per packet. FIGS. 8D, 8E and 8F illustrate one, two and on-half packets per pump stroke, respectively, for four slices per packet. FIGS. 8G and 8H illustrate one and one-half packets per pump stroke, respectively, for three slices per packet. Either two or four elements are included in the switching time offset vector for the illustrated cases.

The second rule is applied when the number of packets per pump stroke is greater than one and the number of slices per packet is an odd number. Similar to the first rule, modulation is performed for the first switching event and every other switching event in a pump stroke. The switching time offsets d are selected as $d_{(st+dsw)}$ from the switching time offset vector where st is the pump stroke number and dsw is the modulated switch number. The value of dsw resets to zero at the start of a pump stroke because the intake response in one intake of the dual head pump system does not have an effect on the following intake stroke at the other intake. An alternative technique is to apply a single switching time offset for each pump stroke; however, this alternative is not preferred as it generates longer term noise than is necessary to achieve the desired error reduction.

Figure 9:
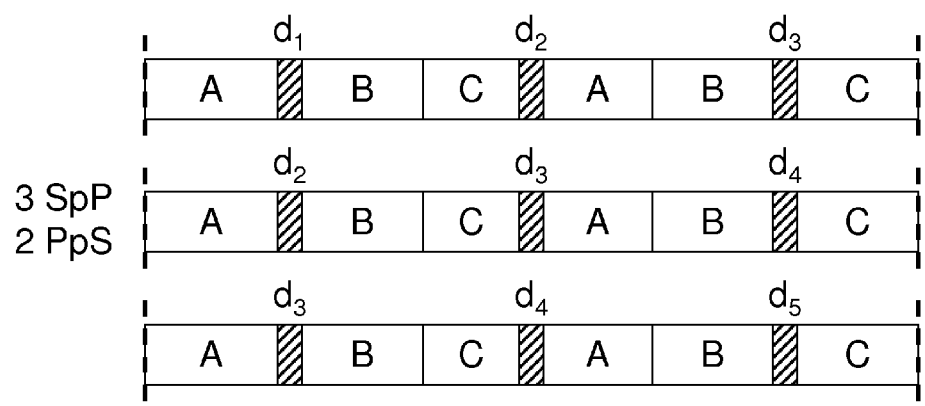
FIG. 9 illustrates the application of an embodiment of the method of the invention according to a second rule for two packets per pump stroke and three slices per packet.

FIG. 9 is an example application of the second rule for a case in which there are two packets per pump stroke and three slices per packet. The first switching occurrence between solvents B and C and the second switching occurrence between solvents A and B in a pump stroke are unmodulated because they are "even-numbered" switching events within the pump stroke. For the first and subsequent "odd-numbered" switching occurrences in a pump stroke the switching time offsets chosen from the switching time offset vector are incremented by one relative to the switching time offsets used in the previous stroke.

Table 1 summarizes how the switching time offsets are applied in a more general sense. The number of switching time offsets that are used is determined by the number n of elements in the vector. When m increases so that it exceeds n, m is reset and the switching time offsets are again used in order of occurrence in the vector beginning with $d_1$.

TABLE 1

| Stroke Number (st) | Modulated Switching Number (dsw) | | | | |
|---|---|---|---|---|---|
| | 1 | 2 | 3 | 4 | m |
| 1 | $d_1$ | $d_2$ | $d_3$ | $d_4$ | $d_m$ |
| 2 | $d_2$ | $d_3$ | $d_4$ | $d_5$ | $d_1 + m$ |
| 3 | $d_3$ | $d_4$ | $d_5$ | $d_6$ | $d_2 + m$ |
| 4 | $d_4$ | $d_5$ | $d_6$ | $d_7$ | $d_3 + m$ |
| n | $d_n$ | $d_n + 1$ | $d_n + 2$ | $d_n + 3$ | $d_n + m$ |

Every switching event and the beginning and the end of pump strokes are occurrences which generally are accounted for when implementing the method of switching time modulation according to the invention. In particular, the minimum time for the actuation of a switch and the available time $T_{AVAIL}$ measured from the unmodulated switching time to the next event, such as the next switching time or the beginning of the next stroke, can limit application of the method. To accommodate such limitations, one embodiment of the method includes scaling, or "collapsing," the vector of switching time offset values.

To decide whether collapsing is to be performed, the available time $T_{AVAIL}$ about a switching time is determined. The value of a parameter K is given by $$K = T_{AVAIL}/\max(\text{abs}(d))$$

where the numerator is the maximum value determined from the absolute values of the switching time offset values in the vector. If K is equal to or greater than one, no collapsing is necessary as the available time $T_{AVAIL}$ accommodates all of the switching time offsets; however, if K is less than one, all elements of the vector are scaled by K so that the width of the switching time modulation range is effectively collapsed. Scaling of the switching offset times ensures that all switching time offsets can be used within the available time $T_{AVAIL}$.

Figure 10A:
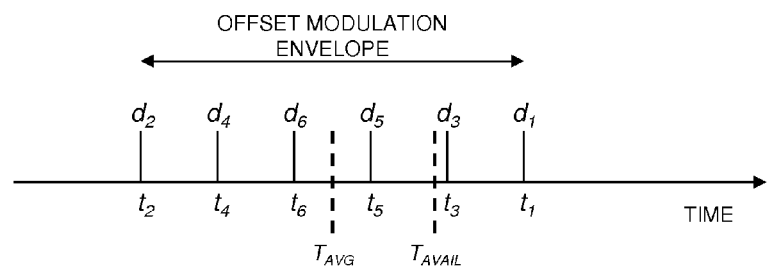
FIG. 10A and FIG. 10B graphically illustrate an example of a timeline for switching events based on switching time modulation and a modified timeline based on a collapsed vector of switching time offset values according to an embodiment of the method of the invention.
Figure 10B:
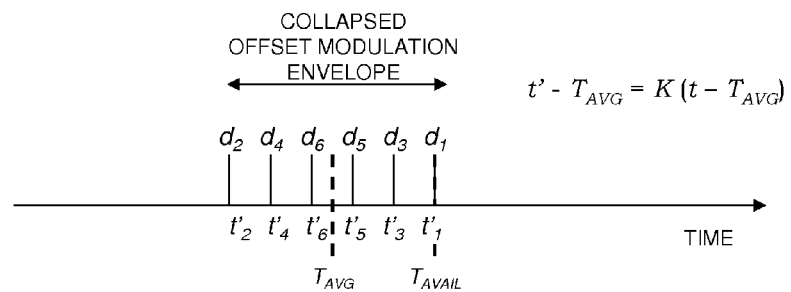

FIG. 10A and FIG. 10B graphically illustrate an example of a timeline for switching events based on switching time modulation and a modified timeline based on a collapsed vector of switching time offset values. In FIG. 10A there are six different switching times $t_1$ to $t_6$ corresponding to six switching time offsets $d_1$ to $d_6$, respectively. The time $T_{AVAIL}$ indicates the latest time in which a switching event is allowed to occur. Times $t_1$ and $t_3$ occur after the expiration of available time therefore the vector of switching time offset values is scaled by the constant K as shown in FIG. 10B so that all possible modulated switching times t' are accommodated in the available time. The value of K is selected such that the full spread of possible switching times based on the vector fits into the available time.

The frequency characteristic of the digital filtering performed with the collapsed switching time offsets scales according to the value of K. An example of this effect can be seen by again referring to FIG. 5 where the modulation observed on the linear gradient 50 is significantly decreased in the lowest and highest concentration regions.

In a preferred embodiment, the commanded switching times for the gradient proportioning valve are advanced (i.e., "time-shifted") to ensure that valve actuation occurs at the proper time to overcome valve delay and thereby provide the desired volumes for the slices. As the pump works in the volume/motor position domain, the time shift is converted to motor steps. To reduce complexity, a constant intake velocity is assumed; therefore positional shift is equal to velocity multiplied by time shift. This assumption yields error when the time shifts occur on the acceleration and deceleration regions of the intake velocity profile. This error is generally small therefore the constant intake velocity assumption is sufficient in most cases.

The above descriptions and embodiments are based on time and a constant pump velocity, therefore the volume variations for each slice due to switching time offset modulation are averaged out. In another preferred embodiment, the switching time offsets are converted into position steps of the pump motor. More specifically, the timing is mapped to stepper motor position to account for variation of the intake volume of the pump in time so that a volumetric average is achieved instead of a switching time offset average. This mapping is important when switching times occur early or late in a pump stroke when the pump velocity is accelerating or decelerating.

While the invention has been shown and described with reference to specific embodiments, it should be understood by those skilled in the art that various changes in form and detail may be made therein without departing from the spirit and scope of the invention as recited in the accompanying claims.

What is claimed is:
1. A method of reducing composition error in an output flow of a mixing pump system, the method comprising:
actuating a first valve during a first packet to provide a first volume of a first component to an intake of the mixing pump system and subsequently actuating a second valve during the first packet to provide a first volume of the second component to the intake of the mixing pump system; and actuating the first valve for at least one subsequent packet to provide, for each subsequent packet, an additional volume of the first component to the intake of the first mixing pump system and subsequently actuating the second valve for each of the at least one subsequent packets to provide an additional volume of the second component to the intake of the mixing pump system, wherein at least two of the first and additional volumes of the first component differ and at least two of the first and additional volumes of the second component differ.

2. The method of claim 1 wherein an average of the first and additional volumes of the first component and an average of the first and additional volumes of the second component equals a respective component volume predetermined to achieve a proportion of a respective component in the output flow.

* * * * *